(12) United States Patent
Ohta et al.

(10) Patent No.: US 7,968,339 B2
(45) Date of Patent: Jun. 28, 2011

(54) METHOD OF INDUCING GENOME REORGANIZATION VIA INTRACELLULAR ACTIVATION OF THERMOSTABLE MULTIFREQUENCY DNA-CLEAVING ENZYME

(75) Inventors: Kunihiro Ohta, Wako (JP); Hidetaka Seo, Tokyo (JP); Kouji Hirota, Tokyo (JP); Takehiko Shibata, Saitama (JP)

(73) Assignee: Riken, Saitama (JP)

( * ) Notice: Subject to any disclaimer, the term of this patent is extended or adjusted under 35 U.S.C. 154(b) by 475 days.

(21) Appl. No.: 11/791,126

(22) PCT Filed: Nov. 22, 2005

(86) PCT No.: PCT/JP2005/021423
§ 371 (c)(1),
(2), (4) Date: Jan. 24, 2008

(87) PCT Pub. No.: WO2006/054766
PCT Pub. Date: May 26, 2006

(65) Prior Publication Data
US 2008/0166809 A1    Jul. 10, 2008

(30) Foreign Application Priority Data
Nov. 22, 2004  (JP) ................................ 2004-338029

(51) Int. Cl.
C12N 15/00 (2006.01)
C12N 5/02 (2006.01)
C12N 5/04 (2006.01)
C12N 5/07 (2006.01)
C12N 1/00 (2006.01)
C12N 1/19 (2006.01)

(52) U.S. Cl. ........ 435/440; 435/455; 435/468; 435/471; 435/325; 435/410; 435/254.11

(58) Field of Classification Search .................... None
See application file for complete search history.

(56) References Cited

U.S. PATENT DOCUMENTS
5,792,633 A  8/1998  Schiestl et al.
6,037,162 A  3/2000  Raveh
6,610,545 B2  8/2003  Dujon et al.

FOREIGN PATENT DOCUMENTS
WO  WO9323534 A1  11/1993

OTHER PUBLICATIONS
Lawyer et al., J. Biol. Chem., 1989; 264:6427-6437.*
Barany, Gene 65:166, 1988.*

Barnes, G., et al. Regulated expression of endonuclease EcoRI in *Saccharomyces cerevisiae*: nuclear entry and biological consequences. Proc. Natl. Acad. Sci. U.S.A. 1985, vol. 82, pp. 1354-1358.
Choulika, A, et al. Induction of homologous recombination in mammalian chromosomes by using the I-Scel system of *Saccharomyces cerevisiae*. Molecular and Cellular Biology. 1995, vol. 15, No. 4, pp. 1968-1973.
Disanto, J., et al. Lymphoid development in mice with a targeted deletion of the interleukin 2 receptor gamma chain. Proc. Natl. Acad. Sci. U.S.A. 1995, vol. 92, pp. 377-381.
Jacquier, et al. An intron-encoded protein is active in a gene conversion process that spreads an intron into a mitochondrial gene. Cell. 1985, vol. 41, pp. 383-394.
Kobayashi, K., et al. Tainetsusei Seigen Koso no Yudo Kasseika nu yoru Taisaibo Sodo Kumikae no Sokushin. Annual Meeting of the Molecular Biology Society of Japan Program, Koen Yoshishu, Nov. 25, 2004, vol. 27th, p. 648, 2PA-187.
Rouet, P., et al. Expression of a site-specific endonuclease stimulates homologous recombination in mammalian cells. Proc. Natl. Acad. Sci. U.S.A. 1994, vol. 91, pp. 6064-6068.
Sadekova, S., et al. Induction of homologous recombination in mammalian chromosomes by using the I-Scel system of *Saccharomyces cerevisiae*. Current Genetics. 1996, vol. 30, No. 1, pp. 50-55.
Schiestl, R., et al. Effect of mutations in genes affecting homologous recombination on restriction enzyme-mediated and illegitimate recombination in *Saccharomyces cerevisiae*. Molecular and Cellular Biology. 1994, vol. 14, pp. 4493-4500.
Schiestl, R., et al. Integration of DNA fragments by illegitimate recombination in *Saccharomyces cerevisiae*. Proc. Natl. Acad. Sci. U.S.A. 1991, vol. 88, pp. 7585-7589.
Toksoy, E., et al. High-level production of TaqI restriction endonuclease by three different expression systems in *Escherichia coli* cells using the T7 phage promoter. Applied Microbiology and Biotechnology. 2002, vol. 59, No. 2-3, pp. 239-245.
Hunt, T., et al. Molecular Biology of the Cell: Third Edition, pp. 1014-1021. 1999. Garland Science. New York. Japanese Version.
Slatko, et al., Cloning, sequencing and expression of the Taq I restriction-modification system., Nucleic Acids Research, 1987, vol. 15, No. 23 9781-9796.

* cited by examiner

*Primary Examiner* — Nancy Vogel
(74) *Attorney, Agent, or Firm* — Carol L. Francis; Bozicevic, Field & Francis LLP

(57) ABSTRACT

The present invention relates to a method for increasing genetic recombination frequency in a genomic DNA and a method for inducing genome rearrangement. Specifically, according to the present invention there are provided: the method for increasing genetic recombination frequency in a cell in which genetic recombination takes place at any sites in the genome, comprising causing a restriction enzyme to be expressed in the cell, inducing transient activation of the restriction enzyme, and then introducing 2 or more double strand cleavages into any genomic DNA of the cell, so as to increase the genetic recombination frequency; the method for inducing genome rearrangement through the use of the above method; and cells each prepared through the use of the above 2 methods.

34 Claims, 5 Drawing Sheets

METHOD OF INDUCING GENOME REORGANIZATION VIA INTRACELLULAR ACTIVATION OF THERMOSTABLE MULTIFREQUENCY DNA-CLEAVING ENZYME

TECHNICAL FIELD

The present invention generally relates to technology for increasing the genetic recombination frequency in genomic DNA. The present invention more specifically relates to a method for inducing genome rearrangement by increasing the genetic recombination frequency in genomic DNA and cells in which genome rearrangement has been carried out by the method.

BACKGROUND ART

Examples of recombinases known to be used in the conventional technology include HO endonuclease (e.g., see the specification of U.S. Pat. No. 6,037,162), I-SceI (for example, see the specification of U.S. Pat. No. 6,610,545; Jacquier et al., 1985. Cell, 41: 383-394; and Rouet et al., 1994. Proc. Natl. Acad. Sci. U.S.A., 91: 6064-6068), and Cre-lox (for example, see DiSanto et al., 1995. Proc. Natl. Acad. Sci. U.S.A. 92: 377-381). These enzymes are of a type of site-specific recombinase that exerts the functions via its introduction into cells. These enzymes extremely strictly recognize sequences and have no cleavage sites in heterologous genomes. These cleavage sequences are previously introduced into genomes, so that only the homologous recombination in the peripheries thereof can be activated. However, unlike the present invention, these enzymes cannot be used in principle for improving recombination frequency in general genomes. Regarding techniques for increasing recombination frequency at general positions in genomes using DNA-cleaving enzymes, no useful systems have been established. This is because the activity of a cleavage enzyme cannot be strictly controlled, thus likely causing a lethal effect on the cells. A similar conventional technique, an REMI method (Restriction Enzyme-Mediated Integration) (e.g., the specification of U.S. Pat. No. 5,792,633; Schiestl and Petes, 1991. Proc. Natl. Acad. Sci. U.S.A. 88: 7585-7589; and Schiestl et al., 1994. Mol. Cell. Biol. 14: 4493-4500) involves, upon transformation, mixing a restriction enzyme with DNA and then introducing the mixture into cells, so as to make it possible to increase the frequency of inserting the introduced DNA into the chromosome. However, with such a technique, DNA and a restriction enzyme can be incorporated into only small number of cells and the enzyme activity cannot be controlled. Hence, the use of such a technique is limited to only the promotion of the insertion of a foreign DNA into a chromosome. These conventional techniques have an essential drawback such that they cannot be used for large-scale genome composition alteration, such as genome shuffling.

DISCLOSURE OF THE INVENTION

Objects to be Achieved by the Invention

In general, an object of the present invention is to provide a method of increasing the genetic recombination frequency in genomic DNA.

Furthermore, an object of the present invention is to provide a method for inducing genome rearrangement.

Furthermore, an object of the present invention is to provide a cell in which the genetic recombination is carried out in genomic DNA by the above method or a cell in which genomic DNA is rearranged by the above method.

Means to Solve the Problems

In view of the above circumstances, the present inventors have thoroughly studied concerning a method for efficiently increasing the genetic recombination frequency in genomic DNA. As a result, the present inventors have surprisingly discovered that a transient increase in intracellular restriction enzyme activity and introduction of double strand cleavages into genomic DNA existing in the cell lead to an efficient increase in genetic recombination frequency in the genomic DNA.

Restriction enzyme activity cannot be controlled by conventional techniques. Hence, unlike the technique of the present invention, it is unable to generate a cell in which a restriction enzyme having many cleavage sites have been previously incorporated in the genome. Therefore, such conventional techniques are extremely inefficient for use in promotion of genome shuffling in microorganisms such as yeast. The use of such conventional techniques is practically impossible. A restriction enzyme Taq I or the like of a thermophile or the like, which is used in the present invention, exerts almost no activity under normal temperature. Therefore, cell survival can be maintained to some extent under conditions where such enzyme is expressed in a large amount. Furthermore, the control of temperatures to be increased and the time therefor makes it possible to regulate recombination frequency. Moreover, Taq I recognizes 4 nucleotides and has many cleavage positions in a genome. Thus, Taq I can be used for improving recombination frequency at any of these positions.

Specifically, the present invention relates to the following (1) to (13).
(1) The invention according to the first embodiment of the present invention is "a method for increasing genetic recombination frequency in a cell, wherein genetic recombination takes place at any sites in the genome, comprising causing a restriction enzyme to be expressed in the cell, inducing transient activation of the restriction enzyme, and introducing 2 or more double strand cleavages at any sites in the genomic DNA of the cell, so as to increase genetic recombination frequency."
(2) The invention according to the second embodiment of the present invention is "the method according to (1) above, wherein the genetic recombination is homologous recombination."
(3) The invention according to the third embodiment of the present invention is "the method according to (1) above, wherein the genetic recombination is non-homologous recombination."
(4) The invention according to the fourth embodiment of the present invention is "the method according to any one of (1) to (3) above, wherein the cell is selected from the group consisting of a fungal cell, a budding yeast cell, and a fission yeast cell."
(5) The invention according to the fifth embodiment of the present invention is "the method according to any one of (1) to (4) above, wherein the restriction enzyme is inducibly expressed."
(6) The invention according to the sixth embodiment of the present invention is "the method according to any one of (1) to (5) above, wherein the number of nucleotides to be recognized by the restriction enzyme is 4."

(7) The invention according to the seventh embodiment of the present invention is "the method according to any one of (1) to (6) above, wherein the restriction enzyme is isolated from a heat-resistant bacterium."
(8) The invention according to the eighth embodiment of the present invention is "the method according to (7) above, comprising increasing the temperature for the cell to a temperature at which the restriction enzyme is activated, incubating the cell at such increased temperature, and thus achieving transient activation of the restriction enzyme."
(9) The invention according to the ninth embodiment of the present invention is "the method according to (8) above, wherein the restriction enzyme is Taq I."
(10) The invention according to the tenth embodiment of the present invention is "the method according to (8) or (9) above, wherein the temperature at which the restriction enzyme is activated ranges from 40° C. to 60° C."
(11) The invention according to the eleventh embodiment of the present invention is "the method according to any one of (8) to (10) above, wherein the incubation is performed for 3 to 30 minutes."
(12) The invention according to the twelfth embodiment of the present invention is "a method for inducing genome rearrangement in the cell, using the method according to any one of (1) to (11) above."
(13) The invention according to the thirteenth embodiment of the present invention is "a cell, which is prepared by the method according to any one of (1) to (12) above."

Effect of the Invention

The use of the present invention makes it possible for almost all cell populations to which the methods according to the present invention are applied to efficiently improve genetic recombination frequency in the genomic DNA.

Furthermore, the application of the methods according to the present invention to a cell makes it possible to induce activation of genetic recombination in the cell at any timing and thus to perform shuffling in the genome of the cell.

Furthermore, the application of the methods of the present invention to various cells makes it possible to perform genome rearrangement via promotion of recombination between homologous chromosomes and thus to perform improvement of the genetic trait relatively easily.

Furthermore, the use of the methods of the present invention makes it possible to promote genome shuffling among cells having different attributes (for example, between yeast for protein expression and yeast with high cohesiveness, soy-sauce yeast and sake brewing yeast, cryoresistant yeast and bread yeast, or various microorganisms existing in extreme environment) and thus to create a cell that has acquired novel characteristics.

BRIEF DESCRIPTION OF THE DRAWINGS

FIG. 5 shows the results of the strain having the PHS141 plasmid incorporated therein and the results of the strain having the Aureobasidin-A-resistant PHS141 plasmid incorporated therein.

PREFERRED EMBODIMENTS OF THE INVENTION

Figure 1:
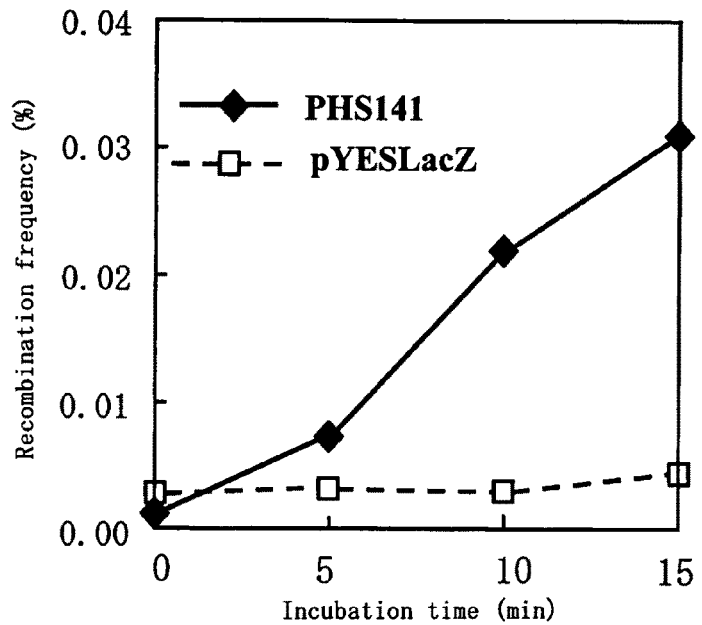
FIG. 1 shows recombination frequency (%) when experimental yeast was cultured in galactose medium for 2 hours and then heated at 50° C. The horizontal axis indicates the time that has elapsed after incubation at 50° C. and the vertical axis indicates recombination frequency (%). Moreover, the solid line indicates the result of a strain in which a PHS141 plasmid has been incorporated and the broken line indicates the result of a strain in which a pYESlacZ plasmid has been incorporated.

As the preferred embodiments for implementing the present invention, a method that involves causing a Taq I gene to be inducibly expressed within yeast cells, transiently activating the restriction enzyme Taq I, and thus increasing genetic recombination frequency is mainly described in detail as follows.

1. Cell

Cells to which the present invention can be applied may be prokaryotic cells or eukaryotic cells, as long as genetic recombination takes place even at low levels in the cells. Such cells can be easily selected by persons skilled in the art. Examples of such cells include, but are not limited to, animal cells, plant cells, fungal cells, and yeast cells. Preferably, fission yeast, budding yeast, and the like can be selected.

Here, "genetic recombination" means, in broad terms, DNA cleavage and recombination phenomena that take place among DNAs. "Genetic recombination" in the present invention includes both homologous recombination and non-homologous recombination. Moreover, "genome rearrangement" means that as "genetic recombination" frequency increases, recombination takes place between the existing genome sequences, so as to cause partial or total changes to occur in the relevant genome sequences.

Culture conditions for cells to be employed in the present invention are achieved by a method known in the art. It goes without saying that cells are cultured using medium and culture conditions (e.g., culture temperature) that are appropriate for the selected cells. Examples of medium include SD medium that is generally used and selection medium for enabling the selection of a transformant using a selection marker. Culture is generally performed at a temperature appropriate for cells to be used (in the case of yeast cells at 30° C., for example) for several days. During culture, antibiotics may be added to medium, when necessary. Furthermore, when a restriction enzyme introduced within a cell is inducibly expressed, an inducible transcription promoter may be used for inducibly carrying out transcriptional control of the restriction enzyme. When such an inducible transcription promoter is used, an agent (e.g., galactose) for inducing transcription may be added.

2. Restriction Enzyme

For implementation of the method according to the present invention, there is a need to transiently activate a restriction enzyme in a cell in which increased genetic recombination frequency is desired and to introduce double strand cleavages at appropriate positions in the genomic DNA. The efficiency of increasing genetic recombination frequency depends on the number of cleavage sites. Hence, enzymes with too many number or too small number of cleavage sites are poorly adequate for use in the method. Examples of restriction enzymes to be used in the method according to the present invention include, but are not limited thereto, preferably a restriction enzyme with a 4- to 6-nucleotide recognition site, further preferably an enzyme with a 4- to 5-nucleotide recognition site, and most preferably an enzyme with a 4-nucleotide recognition site. Moreover, there is a need to be able to "transiently activate" restriction enzymes to be used in the present invention. Here, "transiently activate" means to activate the restriction enzyme for several minutes through several minutes of culture of cells under conditions differing from general culture conditions. Furthermore, "conditions differing from general culture conditions" may be any conditions, as long as such conditions can be selected by persons skilled in the art. For example, conditions wherein a substance (e.g., a metal ion) required for activation of a restriction enzyme used herein is added or temperature conditions (e.g., temperature increase) required for activation of a restriction enzyme used herein can be employed.

For example, when the present invention is applied to budding yeast cells, a preferable restriction enzyme is Taq I. With the use of a method for transiently activating Taq I, yeast cells in which Taq I has been introduced so that expression is possible can be incubated for 1 minute to 30 minutes at 40° C. to 60° C. and more preferably at 50° C.

Furthermore, when the method of the present invention is applied to fission yeast cells, a preferable restriction enzyme is Taq I. With the use of a method for transiently activate Taq I, yeast cells in which Taq I has been introduced so that expression is possible can be incubated for 1 minute to 5 minutes at 40° C. to 60° C. and more preferably at 50° C.

3. Expression of Restriction Enzyme

Restriction enzymes to be used in the method should be expressed within target cells. Preferably, it is desired that the restriction enzymes be inducibly expressed so that expression can be regulated. For regulation of the expression of such restriction enzyme, any method may be used, as long as it is a technique known by persons skilled in the art. Preferably, this can be achieved by constructing an appropriate vector containing a region for carrying out the transcriptional control of such restriction enzyme and the restriction enzyme gene and then introducing the vector into cells. Expression of such restriction enzyme can be induced by maintaining such vector in the form of a plasmid within a target cell. A method that is preferably used herein involves incorporating a region for carrying out the transcriptional control of the restriction enzyme and the restriction enzyme gene into any regions on a chromosome and then causing stable expression of the restriction enzyme and more preferably causing stable and inducible expression thereof. Here, "a region for carrying out the transcriptional control of a restriction enzyme" is a DNA sequence required for the transcriptional control of a specific gene, which is present adjacent to the gene and contains any sequences required for controlling a transcription promoter, an enhancer, and other transcriptional activities.

Any transcription promoters including a constitutive promoter and an inducible promoter can be used. An inducible promoter is preferable since the expression of a restriction enzyme can be controlled. Examples of such inducible promoter include those responding to thiamine deficiency and those responding to galactose. In particular, transcription promoters responding to galactose are preferable.

EXAMPLES

Examples using yeast cells will be described below. However, the present invention is not limited by the following examples.

Examples include 1) cloning of a Taq I gene of a heat-resistant bacterium and construction of an expression vector within budding yeast or fission yeast cells and 2) confirmation of increased levels of recombination due to heat treatment of Taq I-expressing cells. Thus, activation of recombination within yeast is induced at any timing, making it possible to perform shuffling among yeast genomes.

First, a strain inducibly expressing Taq I within diploid yeast cells was established. The cells have nutritional marker genes each having two different point mutations for determination of activation of recombination. As a result of recombination between such point mutation marker genes and the following removal of the mutations, cells may become non-auxotrophic. The proportion of such non-auxotrophic cells is measured, so that activation of recombination is monitored. Through activation of Taq I within cells, induction of intracellular recombination was confirmed.

Example 1

Activation of Recombination in Budding Yeast (1) Preparation of Plasmid for Taq I Expression Cloning of Taq I endonuclease was performed as follows. Amplification was performed with a 50-μl scale using Taq I-Nterm2 (GGAAACATGGCCCCTACACAAGCCC) (SEQ ID NO: 1) and –Taq I-Cterm (CGGGCCGGTGAGGGCT-TCCC) (SEQ ID NO: 2) as primers and a *Thermus Thermophilus* HB8 Genomic DNA Solution (TAKARA SHUZO CO., LTD.) as a template, and Pyrobest DNA polymerase (TAKARA SHUZO CO., LTD.). After heating at 98° C. for 2 minutes, 23 cycles of a reaction cycle consisting of 98° C. for 20 seconds, 63° C. for 30 seconds, and 72° C. for 1 minute were performed. Finally, a reaction was performed at 72° C. for 5 minutes. Subsequently, 0.5 μl of EX Taq (TAKARA SHUZO CO., LTD.) was added, followed by a reaction at 72°

C. for 10 minutes. 10 μl of the thus obtained sample was separated by 1% agarose gel electrophoresis, a band corresponding to the Taq I gene was excised, and then the resultant was purified using a Mini Elute Gel Extraction Kit (Qiagen). In addition, elution from a column was performed using 12 μl of an elution buffer (included in the kit). 4 μl of the eluate was reacted with 1 μl of a pYES2, 1/V5-His-TOPO vector (Stratagene) in the presence of 1 μl of a Salt Solution, thereby performing transformation into a DH10B strain. The obtained colonies were cultured and then a plasmid was extracted by an alkaline method. The sequence of the plasmid was confirmed using a V5 C-term Reverse Primer, a GAL1 Forward Primer (both produced by Stratagene), and an ABI 310 sequencer. The thus obtained plasmid was named pHS141. The use of the vector makes it possible to control Taq I protein expression within yeast using galactose.

(2) Transformation

Experimental budding yeast ORD149 was transformed with the plasmid pHS141 prepared in (1). ORD149 competent cells were mixed with the plasmid pHS141 in vitro and then transformed using a Fast Yeast-Transformation Kit (Geno Technology Inc.). pHS141 has an URA3 selection marker. Transformed cells were selected using selection medium (SD-Ura) from which uracil had been dropped out. Ura+ colonies that had appeared on SD-Ura agar medium were selected.

(3) Measurement of Recombination Frequency

The ORD149 strain in which the plasmid pHS141 selected in (2) had been incorporated was put into and cultured overnight at 30° C. in SD-Ura selection liquid medium. After the cells were cultured to approximately 2 to $3 \times 10^7$ cells/mL, microbial bodies were centrifuged and then washed with sterilized water. The microbial bodies were transferred to galactose selection liquid medium (SD Galactose-Ura) from which uracil had been dropped out. Culture was started again at 30° C. 1 mL of a culture solution was collected before the start of culture in galactose medium and then used as a sample at 0 hour after the start of culture with galactose.

At 2 hours after the start of culture in galactose medium, culture was completed and then 1 mL of a culture solution was collected. The solution was used as a sample at 2 hours after the start of culture with galactose.

The sample at 2 hours after the start of culture in galactose medium was dispensed into test tubes and then incubated at 50° C. for 0 minute, 5 minutes, 10 minutes, and 15 minutes. The culture solution at 0 hour after the start of culture with galactose was used as a control sample showing the standard recombination frequency. Thus, the control sample was not incubated at 50° C.

YPD agar medium and selection agar medium (SD-Arg) from which arginine had been dropped out were coated with the sample at 2 hours after the start of culture and the sample at 0 hour after the start of culture, both of which had been subjected to incubation treatment, followed by 2 to 3 days of culture at 30° C. In YPD agar medium, all the cells that have survived form colonies. However, in SD-Arg agar medium, only the cells that form colonies have undergone recombination because of the expressed protein so as to be Arg+. Hence, recombination frequency can be measured using a proportion of the number of colonies expressed. SD-Arg agar medium was coated with 100 μL of the culture solution, whereas YPD agar medium was coated with the same amount of the culture solution that had been diluted $10^4$ to $10^5$ folds.

In this experiment, yeast transformed by incorporating a plasmid pYESlacZ into the above ORD149 was used as a negative control. A similar experiment was conducted for this yeast and the result was compared with that of pHS141.

The protein Taq I that causes DNA cleavage within yeast cells was expressed due to the plasmid pHS141. The relevant activity became apparent by incubation at 50° C. and then interchromosomal homologous recombination frequency was increased in arg4 heteroalleles (FIG. 1).

(4) Measurement of Recombination Frequency by Temperature

A culture experiment was conducted for 2 hours using an ORD149 strain in which a plasmid pHS141 had been incorporated by the same method as in (3) Measurement of recombination frequency. Thus, samples at 0 hour and 2 hours after the start of culture were prepared. Samples at 2 hours after the start of culture with galactose were incubated at 30° C., 40° C., 45° C., 50° C., and 55° C. for 20 minutes. SD-Arg medium and YPD agar medium were coated with the culture solutions. 2 days later, the number of colonies on culture agar medium was counted, so that recombination frequency was calculated.

Also in this experiment, the same experiment using an ORD149 strain in which a plasmid pYESlacZ had been incorporated as a negative control was also conducted. The measurement result was compared with that of the strain in which the plasmid pHS141 had been incorporated.

Figure 2:
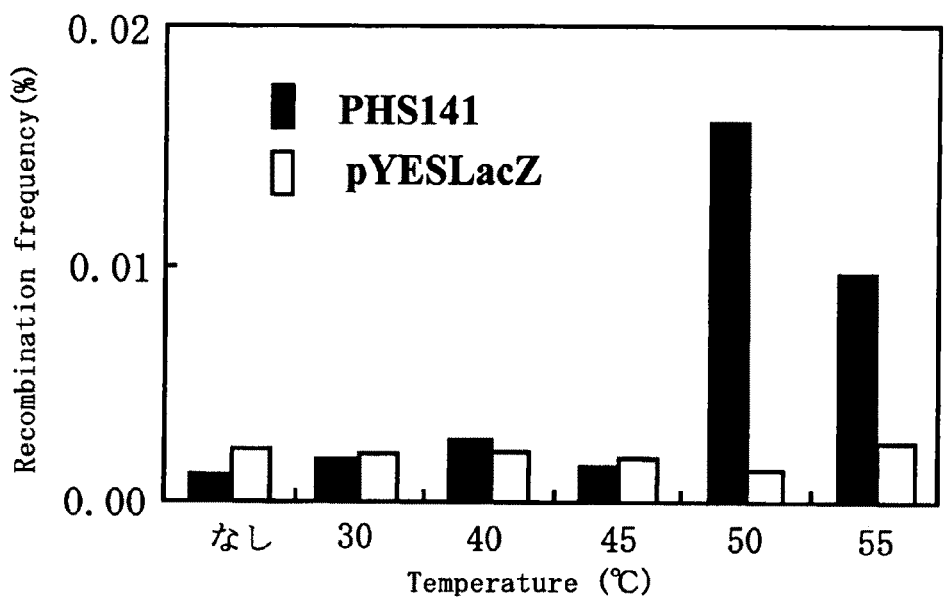
FIG. 2 shows recombination frequency (%) when experimental yeast was cultured in galactose medium for 2 hours and then heated at 30, 40, 45, 50, or 55° C. or not incubated. The vertical axis indicates incubation temperatures and the vertical axis indicates recombination frequency (%). Each black bar indicates the result of a strain in which a PHS141 plasmid has been incorporated and each white bar indicates the result of a strain in which a pYESlacZ plasmid has been incorporated.

In the case of the plasmid pHS141-incorporated strain, the highest increase in recombination frequency was observed upon incubation at 50° C. However, in the case of the negative control strain, no significant increases in recombination frequency were observed (FIG. 2).

(5) Measurement of Appearance Frequency of Adenine-Requiring Yeast

A culture experiment was conducted for 2 hours using an ORD149 strain in which a plasmid pHS141 had been incorporated by the same method as that in (3) Measurement of recombination frequency, thereby collecting culture solutions at 0 hour and at 2 hours after the start of culture. The sample at 2 hours after the start of culture with galactose was incubated at 50° C. for 20 minutes. The culture solution was diluted and adjusted at 1000 to 2000 cells per plate of YPD agar medium. 5 plates were coated with the thus diluted culture solution. The experiment was simultaneously conducted for a negative control (an ORD149 strain in which a plasmid pYESlacZ had been incorporated). Among colonies that had appeared on YPD agar medium, the proportion of red colonies (adenine-requiring yeast in which an ADE2 gene had been disrupted) showing Ade−, that is, indicating the occurrence of recombination, was measured.

Figure 3:
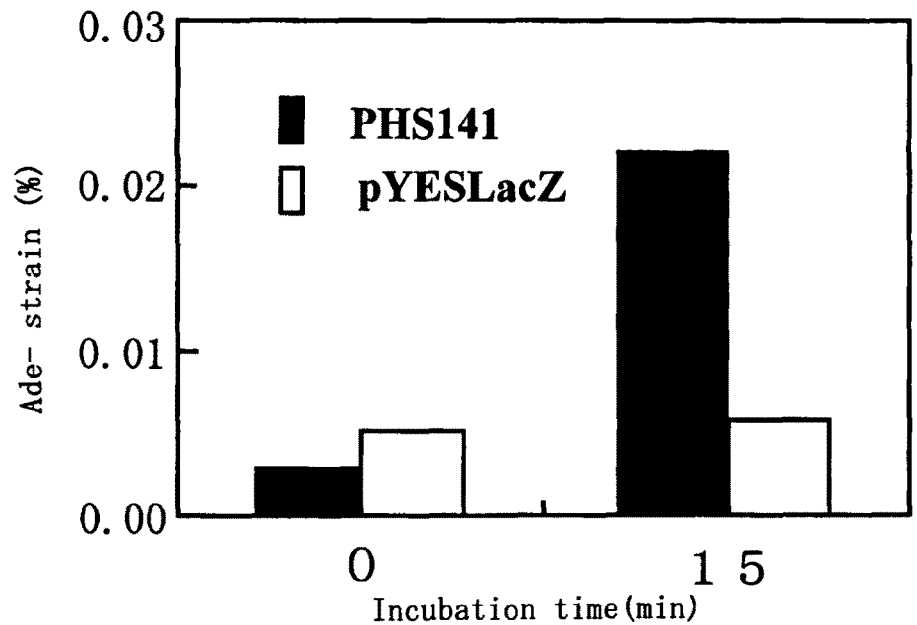
FIG. 3 indicates recombination frequency (%) when experimental yeast was cultured in galactose medium for 2 hours and then heated at 50° C. for 15 minutes or not heated. The horizontal axis indicates the time for heating and the vertical axis indicates recombination frequency (%). Furthermore, each black bar indicates the result of a strain in which a PHS141 plasmid has been incorporated and each white bar indicates the result of a strain in which a pYESlacZ plasmid has been incorporated.

As a result of measurement, it was confirmed that the proportion of Ade− yeast had increased through incubation at 50° C., so that recombination had been induced (FIG. 3).

(6) Measurement of Recombination Frequency in Aureobasidin-Resistant Yeast

Aureobasidin A resistance gene (AUR1) (TAKARA SHUZO CO., LTD.) was inserted into a plasmid pHS141, thereby preparing an expression plasmid (pHS141 Aur+) with Aureobasidin A resistance. The gene was incorporated into an ORD149 strain for transformation. The cells were cultured in SD-Ura medium and then the formed colonies were collected.

Recombination frequency was measured by the same experimental method as in (3) Measurement of recombination frequency.

Figure 4:
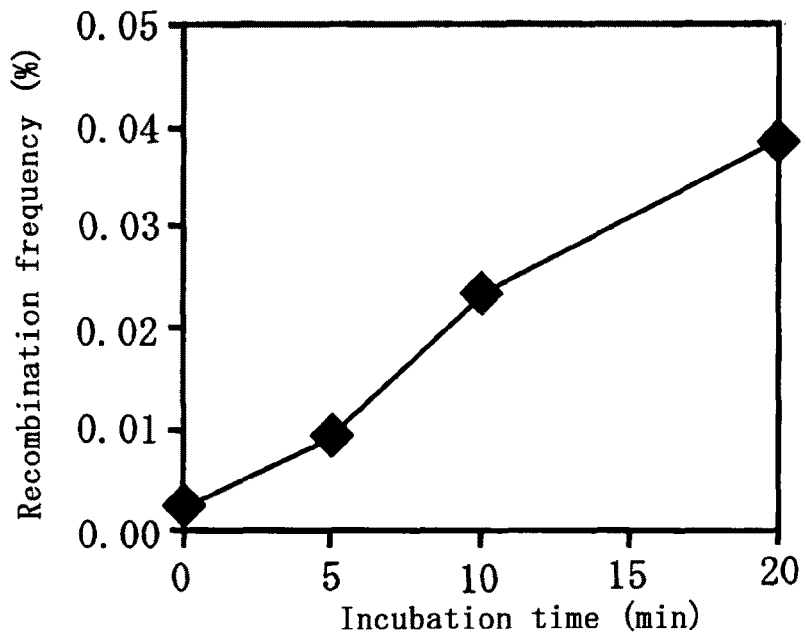
FIG. 4 shows recombination frequency (%) when yeast having an Aureobasidin-A-resistant PHS141 plasmid incorporated therein was cultured in galactose medium for 2 hours and then heated at 50° C. The horizontal axis indicates the time that has elapsed after heating at 50° C. and the vertical axis indicates recombination frequency (%).

As a result of measurement, increases in recombination frequency were confirmed (FIG. 4).

(7) Detection of Expressed Protein

Protein expression induction by galactose was confirmed by the SDS polyacrylamide gel electrophoresis method and the Western blotting method.

Taq I is expressed in a form fused with a V5 tag. Hence, in this experiment, Taq I expression was confirmed using an antibody against the V5 tag.

An ORD149 strain in which a plasmid pHS141 had been incorporated and an ORD149 strain in which a plasmid pHS141 Aur+ had been incorporated were cultured in galactose liquid medium under conditions same as those in (3) Measurement of recombination frequency. However, samples were obtained at 0, 0 5, 1, and 2 hours (4 time points in total) after the start of culture with galactose. Each sample was 1 mL of the culture solution that was not incubated at 50° C. After sample collection, the samples were centrifuged to remove the supernatants. The resultants were washed with pure water and then centrifuged. 500 µl of a Lysis Buffer (50 mM Tris-HCl (pH 8.0), 150 mM NaCl, 1 mM EGTA, and 1 mM MgCl2) was added to the precipitated microbial bodies for suspension. Centrifugation was performed to remove the supernatants. The Lysis Buffer and complete (Roche Diagnostics) in an amount 1/50 thereof were added again to the resultants, followed by suspension.

The suspension was transferred into a tube (exclusively used for a Multi-Beads Shocker) containing 0.6 g of glass beads and then the cells were disrupted by the Multi-Beads Shocker (Yasui Kikai Corporation).

Only an extract was collected from a tube in which cells had been disrupted by low-speed centrifugation. The solution was further centrifuged, so that a precipitate and a supernatant were separately collected.

An SDS polyacrylamide gel electrophoresis sample buffer (containing 2-mercaptoethanol in an amount 1/10 thereof) was added to the precipitate and to the supernatant in an amount equivalent thereto for suspension. The suspensions were incubated at 100° C. for 5 minutes.

Electrophoresis was performed using VX PANTERA Gel SYSTEM (high speed SDS polyacrylamide gel electrophoresis system: DRC CO., LTD.), VX PANTERA Gel (DRC CO., LTD.), and an electrophoresis buffer included therein.

Next, protein detection was performed by the Western blotting method. Current (50 mA and 50 V) was applied to the gel of the electrophoresed sample by a semi-dry method. Proteins were transferred to PVDF membranes (Immobilon Transfer Membranes: Millipore Corporation). A Semi-dry Buffer (25 mM Tris-HCl, pH 8.3, 192 mM Glycine, 20%, methanol or ethanol) was used as an electrophoresis buffer.

Blocking treatment for the PVDF membranes to which proteins had been transferred was performed using a 5% Skim Milk solution dissolved in TBS-T (pH 7.4) (20 mM Tris, 500 mM NaCl, 0.05% Tween). Next, an antibody reaction was performed using a primary antibody Anti V5-Antibody (Invitrogen Corporation). The resultant was washed 3 times with TBS-T, followed by an antibody reaction with a secondary antibody AP α-mouse F(ab')2 (Amersham). The resultant was washed 3 times with TBS-T, and then expressed proteins were detected using a BCIP/NBT Phosphatase Substract (KPL).

Figure 5:
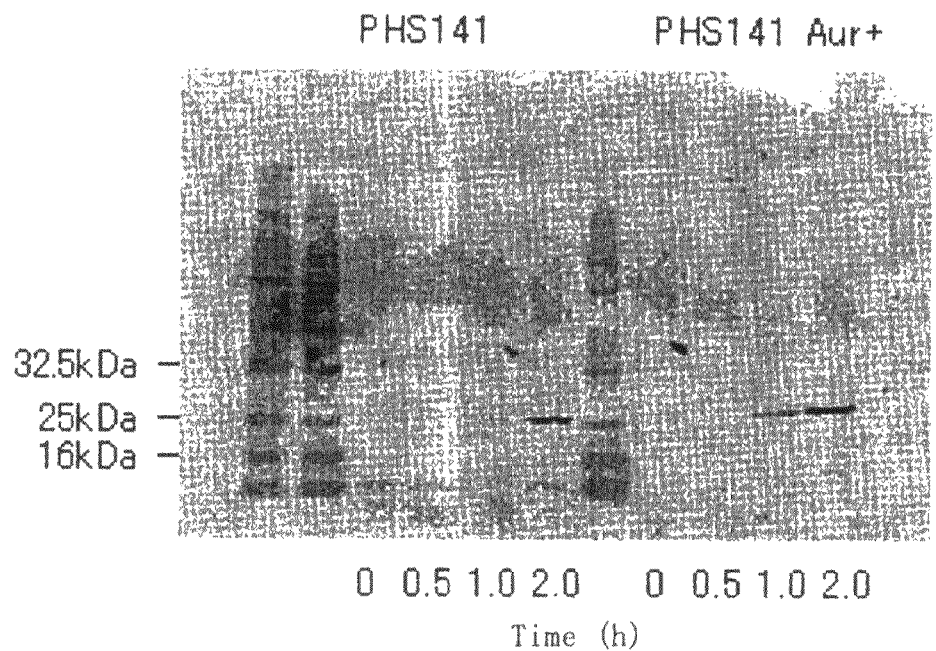
FIG. 5 shows the results of detecting by the Western blotting method proteins expressed by yeast in which a PHS141 plasmid has been incorporated. Specifically, yeast having the PHS141 plasmid incorporated therein was cultured in galactose medium, the microbial bodies were disrupted at 0, 0.5, 1.0, or 2.0 hours after the start of culture, extracts were subjected to SDS-PAGE electrophoresis, the resultants were transferred to membranes by the Western blotting method, and then the proteins were stained.

After SDS-PAGE, it was confirmed by the Western blotting method that pHS141 expressed the Taq I-derived protein (FIG. 5).

Example 2

Activation of Recombination Within Fission Yeast (1) Preparation of D50 Strain

A Taq I gene fragment was obtained by a PCR reaction using the genome of a heat-resistant bacterium as a template and the following oligo DNA.

```
cccCATATGGCCCCTACACAAGCCC        (SEQ ID NO: 3)
(Underlined portion indicates an Nde I
restriction enzyme recognition site)

cccGGATCCTCACGGGCCGGTGAGGGC      (SEQ ID NO: 4)
(Underlined portion indicates a BamH I
restriction enzyme recognition site)
```

The sequence of thus obtained fragment was confirmed and then cleaved with Nde I-BamH I. The fragment is referred to as Taq I-FR. A fission yeast transcription promoter nmt1, TaqIFR, transcription terminator, KanR (geneticin resistance marker gene), fission yeast leu1 gene 3' fragment, and pUC118 were linked and circularized in this order, thereby obtaining an intL-Taq I plasmid. intL-Taq I was cleaved at the Xho I site within the leu1 gene. The resultant was transformed into a fission yeast strain D26. Transformation and obtainment of a geneticin resistance transformant were performed according to the methods described in Hirota et al., Genes to Cells, 6: 201-214, 2001.

This strain can control Taq I protein expression through thiamine removal from medium.

(2) Measurement of Recombination Frequency

The D50 strain was streaked on SD medium (containing thiamine) and then cultured until single colonies appeared. The single colonies were suspended in MM+N liquid medium (not containing thiamine) and then cultured at 30° C. for 16 hours. After the single colonies were cultured to approximately $1 \times 10^7$ cells/ml, microbial bodies were centrifuged. The microbial bodies were washed with sterilized water. The microbial body sample was dispensed in test tubes and then incubated at 50° C. for 0 minute, 1 minute, 3 minutes, and 5 minutes. Similar procedures were performed for the D26 strain not expressing Taq I as a control.

A YE plate and selection medium (SD-ade) from which adenine had been dropped out were coated with the incubated D50 sample and the incubated D26 sample, followed by 7 to 10 days of culture at 30° C.

Whereas all the cells that have survived form colonies on such an YE plate, only the cells that have undergone recombination to be ade+ form colonies on such an SD-ade plate. Hence, recombination frequency can be measured based on the proportion of the number of colonies expressed. SD-ade was coated with 100 µl of each culture solution and YE was coated with the same amount of the culture solution that had been diluted $10^4$ to $10^4$ folds.

Figure 6:
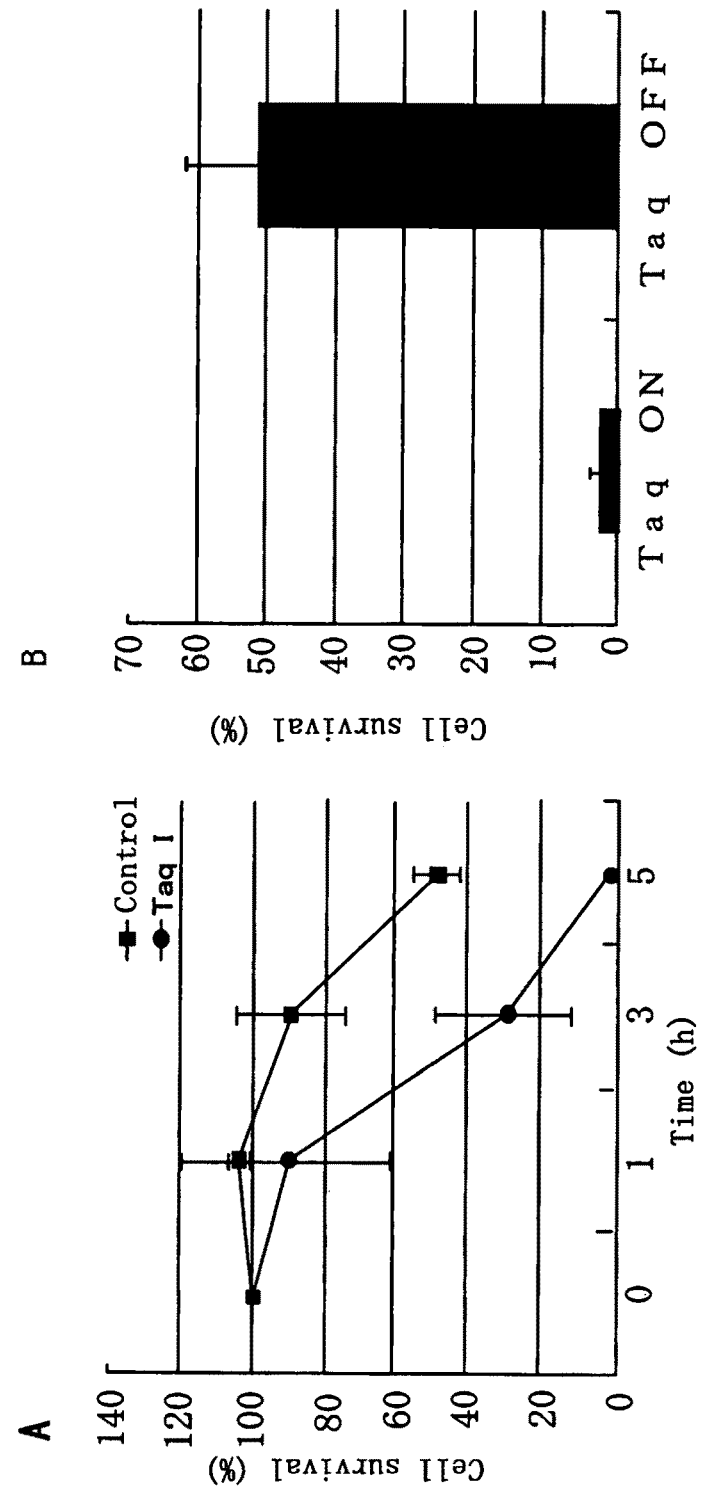
FIG. 6 shows the existence (%) of viable cells at 0, 1, 3, and 5 minutes after heating cells D50 expressing Taq I and cells D26 not expressing Taq I. The survival (%) at "0 minute" is determined to be 100%.

As a result of the experiment, when the temperature was increased after protein expression, significant number of cells died compared with the case of budding yeast, but still many cells survived (FIGS. 6A and B).

Figure 7:
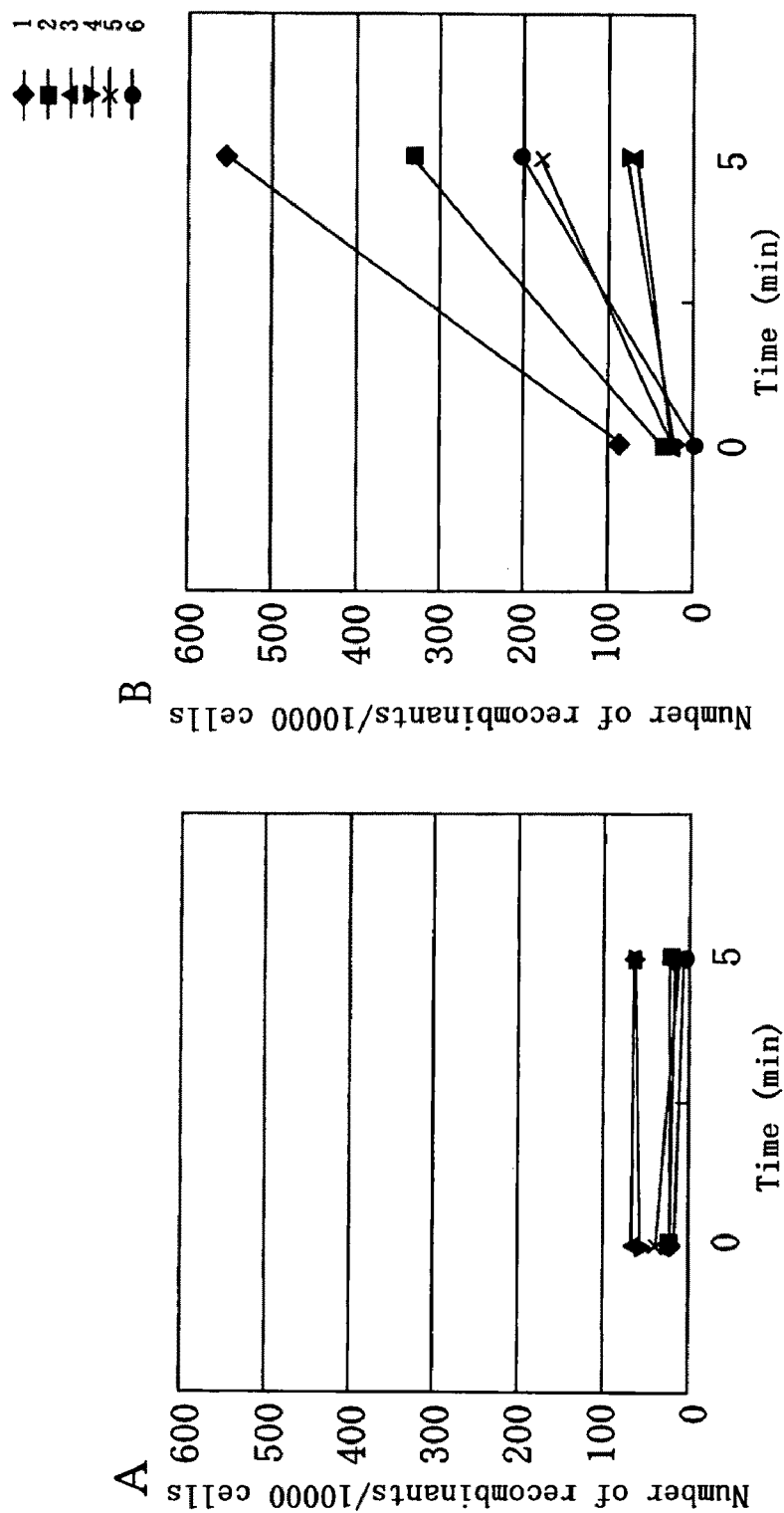
FIG. 7 shows the results of heating cells D50 expressing Taq I and cells D26 not expressing Taq I at 50° C., coating YE and SD-ade plates with the cells at 0 and 5 minutes after heating, and then examining the proportions of recombinants in cells that have survived. Furthermore, "1 to 6" in each graph are numbers assigned to 6 plates used for the experiment, for convenience.

When Taq I-expressing cells were transiently (for 5 minutes) heated, a significant increase in homologous recombination frequency (hundred fold) was observed. In addition, this frequency was equivalent to that in the case of the meiotic phase characterized by the highest homologous recombination frequency (FIG. 7).

3. The method according to claim 1, wherein the temperature at which the restriction enzyme is activated ranges from 40° C. to 60° C.

4. The method according to claim 1, wherein the incubation is performed for 3 to 30 minutes.

---

---

The invention claimed is:

1. A method for increasing genetic recombination frequency in a cell, wherein genetic recombination takes place at any site in the genome, comprising
   incubating a cell comprising a recombinant gene encoding a restriction enzyme of a heat-resistant bacterium said incubating being at an increased temperature to provide transient activation of the restriction enzyme by the cell; wherein said incubating provides for introduction of two or more double stranded cleavages in the genomic DNA of the cell, and wherein genetic recombination frequency in the cell is increased as compared to genetic recombination frequency prior to said incubating.

2. The method according to 1, wherein the restriction enzyme is Taq I.

5. The method according to claim 1, wherein the genetic recombination is homologous recombination.

6. The method according to claim 1, wherein the genetic recombination is non-homologous recombination.

7. The method according to claim 1, wherein the cell is selected from a group consisting of a fungal cell, a budding yeast cell, and a fission yeast cell.

8. The method according to claim 1, wherein the restriction enzyme is inducibly expressed.

9. The method according to claim 1, wherein the number of nucleotides that are recognized by the restriction enzyme is four.

10. A method for inducing genome rearrangement in a cell comprising:
   incubating a cell comprising a recombinant gene encoding a restriction enzyme of a heat-resistant bacterium, said incubating being at an increased temperature to provide transient activation of the restriction enzyme expressed by the cell;

wherein said incubating provides for introduction of two or more double stranded cleavages in the genomic DNA of the cell, and wherein genome rearrangement in the cell is induced.

11. The method according to 10, wherein the restriction enzyme is Taq I.

12. The method according to claim 10, wherein the temperature at which the restriction enzyme is activated ranges from 40° C. to 60° C.

13. The method according to claim 10, wherein the incubation is performed for 3 to 30 minutes.

14. The method according to claim 10, wherein the genetic recombination is homologous recombination.

15. The method according to claim 10, wherein the genetic recombination is non-homologous recombination.

16. The method according to claim 10, wherein the cell is selected from a group consisting of a fungal cell, a budding yeast cell, and a fission yeast cell.

17. The method according to claim 10, wherein the restriction enzyme is inducibly expressed.

18. The method according to claim 10, wherein the number of nucleotides that are recognized by the restriction enzyme is four.

19. A method for producing a cell that has undergone genomic rearrangement, the method comprising:

incubating a cell comprising a recombinant gene encoding a restriction enzyme of a heat-resistant bacterium, said incubating being at an increased temperature to provide transient activation of the restriction enzyme expressed by the cell;

wherein said incubating produces a cell having two or more double stranded cleavages in the genomic DNA of the cell to produce a cell, and wherein genome rearrangement in the cell is induced.

20. The method according to 19, wherein the restriction enzyme is Taq I.

21. The method according to claim 19, wherein the temperature at which the restriction enzyme is activated ranges from 40° C. to 60° C.

22. The method according to claim 19, wherein the incubation is performed for 3 to 30 minutes.

23. The method according to claim 19, wherein the genetic recombination is homologous recombination.

24. The method according to claim 19, wherein the genetic recombination is non-homologous recombination.

25. The method according to claim 19, wherein the cell is selected from a group consisting of a fungal cell, a budding yeast cell, and a fission yeast cell.

26. The method according to claim 19, wherein the restriction enzyme is inducibly expressed.

27. The method according to claim 19, wherein the number of nucleotides that are recognized by the restriction enzyme is four.

28. A cell produced in accordance with the method of claim 10, wherein said cell is a eukaryotic cell.

29. The cell according to claim 28, wherein the cell is a fungal cell.

30. The cell according to claim 29, wherein the restriction enzyme is inducibly expressed.

31. A cell produced in accordance with the method of claim 28, wherein the cell is a budding yeast cell.

32. The cell according to claim 31, wherein the restriction enzyme is inducibly expressed.

33. A cell produced in accordance with the method of claim 28, wherein the cell is a fission yeast cell.

34. The cell according to claim 33, wherein the restriction enzyme is inducibly expressed.

\* \* \* \* \*

SEQUENCE LISTING

```
<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1
ggaaacatgg cccctacaca agccc                                    25

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2
cgggccggtg agggcttccc                                          20

<210> SEQ ID NO 3
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 3
ccccatatgg cccctacaca agccc                                    25

<210> SEQ ID NO 4
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 4
cccggatcct cacgggccgg tgagggc                                  27
```